United States Patent [19]

Tao

[11] Patent Number: 4,810,654
[45] Date of Patent: Mar. 7, 1989

[54] METHOD FOR THE CONCENTRATION DETERMINATION OF SILANE GAS IN A GASEOUS MIXTURE

[75] Inventor: Hiroaki Tao, Ibaraki, Japan

[73] Assignee: Agency of Industrial Science & Technology, Tokyo, Japan

[21] Appl. No.: 921,333

[22] Filed: Oct. 21, 1986

[30] Foreign Application Priority Data

Nov. 9, 1985 [JP] Japan ................. 60-251751

[51] Int. Cl.4 .............. G01N 33/00; G01N 21/00; G01N 7/00
[52] U.S. Cl. .................... 436/72; 436/164; 472/83
[58] Field of Search .............. 436/72, 164, 165, 166; 422/83

[56] References Cited

PUBLICATIONS

Tao et al., Light Scattering Method Combined with Production of Fine Particles by Photochemical Reaction for Determination of Silane in Air, 5/86, pp. 1148-1152.

Primary Examiner—Barry S. Richman
Assistant Examiner—Lyle Alfandary-Alexander
Attorney, Agent, or Firm—Hopgood, Calimafde Kalil, Blaustein Judlowe

[57] ABSTRACT

A very sensitive and reliable analytical method is proposed for the concentration determination of silane $SiH_4$ in a gaseous mixture. In the method, the sample gas is admixed with ozone and irradiated with ultraviolet of a wave length of 200 to 320 nm so that a silicic aerosol is formed in the sample gas and the concentration of the silicic aerosol suspended in the sample gas is determined by the measurement of light scattering. Instead of the admixture of ozone, the sample gas containing or admixed with oxygen is first irradiated with ultraviolet of shorter than 200 nm wave length to convert the oxygen into ozone in situ and then the photochemical formation of silicic aerosol and light scattering measurement are undertaken as mentioned above.

8 Claims, 1 Drawing Sheet 4,810,654

METHOD FOR THE CONCENTRATION DETERMINATION OF SILANE GAS IN A GASEOUS MIXTURE

BACKGROUND OF THE INVENTION

The present invention relates to a method for the determination of the concentration of silane gas in a gaseous mixture or in the atmospheric air or, more particularly, to a method for the determination of a relatively low concentration of silane gas in a working gaseous mixture or in the atmospheric air of the working environment as is sometimes used or encountered in the manufacturing process of semiconductor devices.

As is well known, silane $SiH_4$ is an important material used in a gaseous form in various processes of manufacturing of semiconductor devices. Accordingly, it is important to accurately determine the concentration of silane in a working gas used in the process. ue to the high vapor pressure, furthermore, it is usual that the atmospheric air of the working environment using silane contains the silane more or less so that, in view of the toxicity and inflammability thereof, it is eagerly desired in the semiconductor industry to develop a simple and highly sensitive method for the determination of the silane gas in a gaseous mixture or in air in a relatively low concentration capable of giving reliable results.

Several methods therefor are already known and practiced in the prior art including (1) the electrochemical sensor method using, for example, a membrane Galvani cell or potentiostatic electrolytic cell utilizing the oxidation-reduction reaction of the gas on the surface of the electrode, (2) the chemical reaction-atomic absorption spectrophotometric method in which the silane gas is reacted with mercury oxide to reduce the mercury oxide into vapor of metallic mercury of which the concentration is determined by the atomic absorption spectrophotometry and converted into the concentration of the silane gas, and (3) the chemical luminescence method utilizing the luminescence emitted by the reaction of the silane gas and ozone. These prior art methods, however, have problems and are not quite satisfactory from the standpoint of practice because the sensitivity is not always high enough, selectivity is poor and strongly toxic reagents must be used.

The inventor has previously proposed an apparatus for the concentration determination of several kinds of reactive gases, such as arsine, phosphine, stibine, germane and selenium hydride, used in the processing of semiconductor devices in air, of which the principle of determination utilizes the scattering of light by the fine suspended particles in the air produced when a gaseous mixture of the reactive gas and oxygen is irradiated with ultraviolet. This apparatus and the method, however, are not applicable to the concentration determination of silane gas in a gaseous mixture because the principle thereof is the irradiation of a gaseous mixture of the reactive processing gas and oxygen with ultraviolet, by which the silane gas is not rapidly reacted with oxygen, especially, when the concentration thereof is low.

SUMMARY OF THE INVENTION

An object of the present invention is therefore to provide an improved method for the determination of silane gas in a gaseous mixture or in air without the problems and disadvantages in the prior art methods.

Thus, the method of the present invention for the determination of silane gas contained in a gaseous mixture comprises the steps of:

(a) mixing the silane-containing gaseous mixture with ozone;

(b) irradiating the silane-containing gaseous mixture mixed with ozone with ultraviolet light having a wave length in the range from 200 to 320 nm to produce a silicic aerosol suspended in the gaseous mixture; and (c) measuring scattering of light projected through the gaseous mixture by the silicic aerosol suspended therein.

In a convenient embodiment of the above described method, the ozone to be mixed with the silane-containing gaseous mixture is produced in situ by irradiating a mixture of the silane-containing gas and oxygen with ultraviolet light having a wave length shorter than 200 nm prior to the irradiation with ultraviolet of the wave length of 200 to 320 nm.

DETAILED DESCRIPTION OF THE PREFERRED EMBODIMENTS

Figure 1:
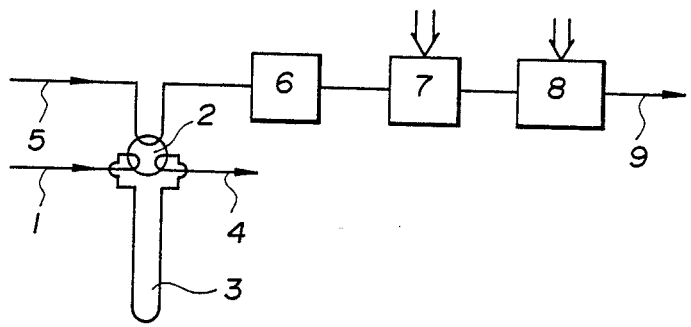
FIG. 1 is a block diagram showing the principle of the inventive method.

As is understood from the above given summarizing description, the principle of the inventive method is the measurement of the light scattering by a silicic aerosol produced when a gaseous mixture containing silane and ozone is irradiated with ultraviolet of the so-called Hartley band of ozone having a wave length of 200 to 320 nm. This method is highly sensitive and reliable in comparison with the above described prior art methods. Further, the efficiency of the inventive analytical method can be improved by producing the ozone in situ by irradiating a gaseous mixture containing silane and oxygen with ultraviolet having a wave length shorter than 200 nm prior to the irradiation with ultraviolet of 200 to 320 nm wave length.

To explain the principle of the inventive method, a part of the silane reacts with ozone first to form critical nuclei of silica. When the gaseous mixture containing ozone is irradiated with ultraviolet of the wave length of 200 to 320 nm, the ozone molecules are photochemically activated to form active species of $O(^1D_2)$ according to the reaction equation $$O_3 + h\nu \rightarrow O_2\,(^1\Delta) + O(^1D_2).$$

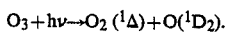

Those active species of oxygen $O_2(^1\Delta)$ or $O(^1D_2)$ react with the unreacted silane $SiH_4$ to form an active intermediate species which causes growth of silica particles into a silicic aerosol upon collision at the surface of the surface of the critical nuclei of silica. When light is projected through the gaseous mixture containing the silicic aerosol, the light is scattered by the silica particles and the degree of light scattering can be correlated to the concentration of the silicic aerosol and hence to the concentration of silane in the gaseous mixture.

The growth of the silica particles takes place by the reaction at the surface of the silica nuclei. This particle growth of silica proceeds even at room temperature. This is a quite unexpected discovery since, as is generally understood, formation of fine particles of a metal or a metal oxide by the collision of critical nuclei can take place only when the temperature given in absolute temperature is higher than 0.3 to 0.4 times of the melting point in absolute of the metal or oxide so that it may be a fair presumption that the particle growth of silica having a melting point of 1940 K could proceed only at about 600 K or higher.

In performing the method of the invention, the sample gas containing silane is admixed with ozone prior to irradiation with ultraviolet. The concentration of ozone in the gaseous mixture under the ultraviolet irradiation should be at least 1% by volume or, preferably, at least 2% by volume. When the concentration of ozone is too low, the velocity of particle growth of the silicic aerosol may be unduly low resulting in a considerable analytical error in the concentration of the silane gas. The ultraviolet irradiation can be performed by using any of known ultraviolet lamps provided that the lamp emits ultraviolet light in a sufficient intensity having a wave length in the range from 200 to 320 nm. It should be noted here that, when the lamp emits ultraviolet light of which the wave length covers both of the ranges longer than and shorter than 200 nm as is the case with mercury lamps, the ultraviolet light irradiating the gaseous mixture should be filtered to eliminate the light having wave lehgths shorter than 200 nm as completely as possible since the irradiation with ultraviolet in both of the wave length ranges simultaneously may cause a considerable error in the analytical results although the mechanisms for this phenomenon is not yet well understood.

As is known, oxygen is converted to ozone when it is irradiated with so-called far ultraviolet having a wave length shorter than 200 nm so that the inventive method can be performed conveniently by first irradiating the silane-containing gaseous mixture containing or admixed with oxygen with far ultraviolet of a wave length shorter than 200 nm to produce ozone in situ and then irradiating the gaseous mixture with ultraviolet of a wave length of 200 to 320 nm followed by the measurement of light scattering. Although no oxygen gas need not be added to the sample gas as a matter of course when the sample gas is the atmospheric air containing silane, non-oxygen sample gases should be admixed prior to irradiation with ultraviolet of the wave length shorter than 200 nm with oxygen in a volume sufficient to produce ozone in a concentration of at least 1% by volume or, preferably, at least 2% by volume upon irradiation with ultraviolet. Various kinds of ultraviolet lamps can be used in the irradiation of the oxygen-admixed sample gas for the in situ formation of ozone provided that the lamp emits ultraviolet in the wave length range shorter than 200 nm in a sufficient intensity. When the lamp emits ultraviolet light having wave lengths in both of the ranges longer than and shorter than 200 nm as is the case with mercury lamps, it is preferable to eliminate the ultraviolet having a wave length of 200 nm or longer as completely as possible.

In the following, the method of the invention is described in more detail with reference to the accompanying drawing. FIG. 1 illustrates a block diagram of the inventive photochemical method for the concentration determination of silane, in which the sample gas containing silane is led through the pipe line 1 and the six-way cock 2 to fill the gas sampler 3 evacuated in advance through the vacuum line 4. It is of course optional that, instead of the above mentioned preliminary evacuation, the gas sampler 3 is filled with the sample gas by continuously passing the sample gas therethrough until complete replacement of the air inside with the sample gas. Then, the mix-way cock is turned to expel the sample gas in the sample holder 3 with the ozone gas introduced through the pipe line 5 as a carrier gas into the mixing cell 6. When the gaseous mixture has been uniformized in the mixing cell 6, the gaseous mixture is led into the photochemical reaction cell 7 where it is irradiated through a quartz glass window with ultraviolet light coming from a xenon lamp of 150 watts output (not shown in the figure) as the light source so that a silicic aerosol is formed in the gaseous mixture. The light source is not limited to xenon lamps but may be any lamps capable of emitting ultraviolet of 200 to 320 nm wave length such as mercury lamps and $D_2$ lamps. The gaseous mixture containing the silicic aerosol is then introduced into the light-scattering photometer 8 having a helium-neon laser or a xenon lamp as the light source to determine scattering of light followed by discharge of the gas out of the system through the gas outlet 9. The light source in the light-scattering photometer should desirably emit light in the wave length range from 200 to 700 nm in consideration of the intensity of light scattering and detecting sensitivity of the detectors and may be an argon laser, semiconductor laser or mercury lamp, of which helium-neon lasers and mercury lamps are preferred although semiconductor lasers emitting light of the wave length of about 800 nm can also be used in respect of the compactness and inexpensiveness of the apparatus. The detector in the light-scattering photometer may be a photomultiplier or a photodiode.

Figure 2:
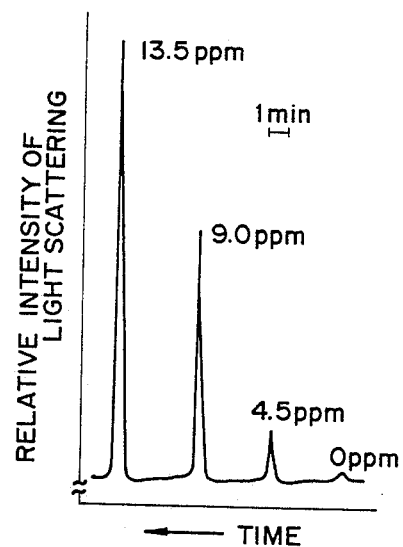
FIG. 2 is an example of the chart showing the intensity of light scattered by a gaseous mixture containing the silicic aerosol produced from silane in different concentrations.

FIG. 2 is an example of the chart obtained in the light-scattering measurement for the concentration determination of silane in air, in which the volume of the sample gas containing 4.5, 9.0 or 13.5 ppm of silane was 1 ml, the light source in each of the photochemical reaction cell 7 and the light-scattering photometer was a xenon lamp of 150 watt output with a photomultiplier as the detector in the light-scattering photometer. As is understood from this figure, the sensitivity of the method is high enough even when the concentration of silane in air is 4.5 ppm or lower, i.e. well below the permissible upper limit of 5 ppm of silane in the environmental atmosphere.

As is mentioned before, the ozone for the photochemical reaction with silane may be produced in situ by irradiating the silane-containing gaseous mixture with admixture of oxygen with far ultraviolet having a wave length shorter than 200 nm emitted from a light source such as mercury laps. When the silane-containing sample gas is atmospheric air, the sample gas as such may be irradiated with far ultraviolet to convert the oxygen in air into ozone. In this case, the sample gas is first irradiated with far ultraviolet in an ozonization cell prior to introduction into the photochemical reaction cell.

What is claimed is:

1. A method for the determination of the concentration of silane gas contained in a gaseous mixture which comprises the steps of:
   (a) mixing the silane-containing gaseous mixture with ozone;
   (b) irradiating the silane-containing gaseous mixture mixed with ozone with ultraviolet light having a wave length in the range from 200 to 320 nm to produce a silicic aerosol suspended in the gaseous mixture; and (c) measuring scattering of light projected through the gaseous mixture by the silicic aerosol suspended therein.

2. A method for the determination of the concentration of silane gas contained in a gaseous mixture which comprises the steps of:
   (a) mixing the silane-containing gaseous mixture with oxygen;
   (b) irradiating the oxygen-admixed silane-containing gaseous mixture with ultraviolet light having a wave length shorter than 200 nm to convert the oxygen into ozone;
   (c) irradiating the silane- and ozone-containing gaseous mixture with ultraviolet light having a wave length in the range from 200 to 320 nm to produce a silicic aerosol suspended in the gaseous mixture; and
   (d) measuring scattering of light projected through the gaseous mixture by the silicic aerosol suspended therein.

3. The method for the determination of the concentration of silane gas contained in a gaseous mixture as claimed in claim 1 wherein the ozone is admixed with the silane-containing gaseous mixture in a concentration of at least 1% by volume.

4. The method for the determination of the ooncentration of silane gas contained in a gaseous mixture as claimed in claim 1 wherein the ultraviolet light used in the step (b) is substantially free from light having a wave length shorter than 200 nm.

5. The method for the determination of the concentration of silane gas contained in a gaseous mixture as claimed in claim 2 wherein the silane-containing gaseous mixture is admixed with the oxygen in the step (a) in such a volume that the concentration of the ozone produced in the step (b) is at least 1% by volume.

6. The method for the determination of the concentration of silane gas contained in a gaseous mixture as claimed in claim 2 wherein the ultraviolet light used in the step (b) is substantially free from light having a wave length of 200 nm or longer.

7. The method for the determination of the concentration of silane gas contained in a gaseous mixture as claimed in claim 2 wherein the ultraviolet light used in the step (c) is substantially free from light having a wave length shorter than 200 nm.

8. A method for the determination of.the concentration of silane gas contained in air which comprises the steps of:
   (a) irradiating the silane-containing air with ultraviolet light having a wave length shorter than 200 nm to convert a part of oxygen in the air into ozone;
   (b) irradiating the silane- and ozone-containing air with ultraviolet light having a wave length in the range from 200 to 320 nm to produce a silicic aerosol suspended in the air: and
   (c) measuring scattering of light projected through the air by the silicic aerosol suspended therein.

* * * * *